United States Patent [19]

Apffel

[11] Patent Number: 4,584,006
[45] Date of Patent: Apr. 22, 1986

[54] PROCESS FOR RECOVERING PROPANE AND HEAVIER HYDROCARBONS FROM A NATURAL GAS STREAM

[75] Inventor: Fred Apffel, Houston, Tex.

[73] Assignee: Flexivol, Inc., Houston, Tex.

[21] Appl. No.: 538,290

[22] Filed: Oct. 3, 1983

Related U.S. Application Data

[63] Continuation-in-part of Ser. No. 356,918, Mar. 10, 1982, Pat. No. 4,456,460.

[51] Int. Cl.$^4$ ................................................. F25J 3/02
[52] U.S. Cl. .......................................... 62/30; 62/31; 62/34; 62/40
[58] Field of Search ..................... 62/40, 9, 11, 23–34, 62/42

[56] References Cited

U.S. PATENT DOCUMENTS 3,747,359  7/1973  Streich .................................. 62/40

Primary Examiner—Frank Sever
Attorney, Agent, or Firm—David M. Ostfeld

[57] ABSTRACT

A process for economically recovering propane and heavier hydrocarbon components from ethane, methane and lighter constituents of natural gas streams is disclosed. The separation process of the natural gas stream is accomplished in two stages. The input gas stream (101) is first cooled by exchanger (301) using various streams of refrigerant. After cooling the stream (102) is partially condensed in a series of separators (109, 111, 112), with part of the ethane, methane and almost all of the propane and heavier hydrocarbons within the stream being condensed. The condensed mixtures (124) are fed to a fractionation tower (113), where the ethane, methane and lighter gases are distilled from the other hydrocarbons. The cooling and condensation of the hydrocarbons in the feed stream and the heat source for the tower (113) are accomplished in indirect contact heat exchangers (301, 302, 303, 304) with a refrigerant and hot oil. The cooling of the feed stream is also accomplished by flashing of the process gases in the separators. The refrigerant utilizes a mixture of hydrocarbons with the refrigerant process comprising compression, condensation, expansion and evaporation.

6 Claims, 1 Drawing Figure

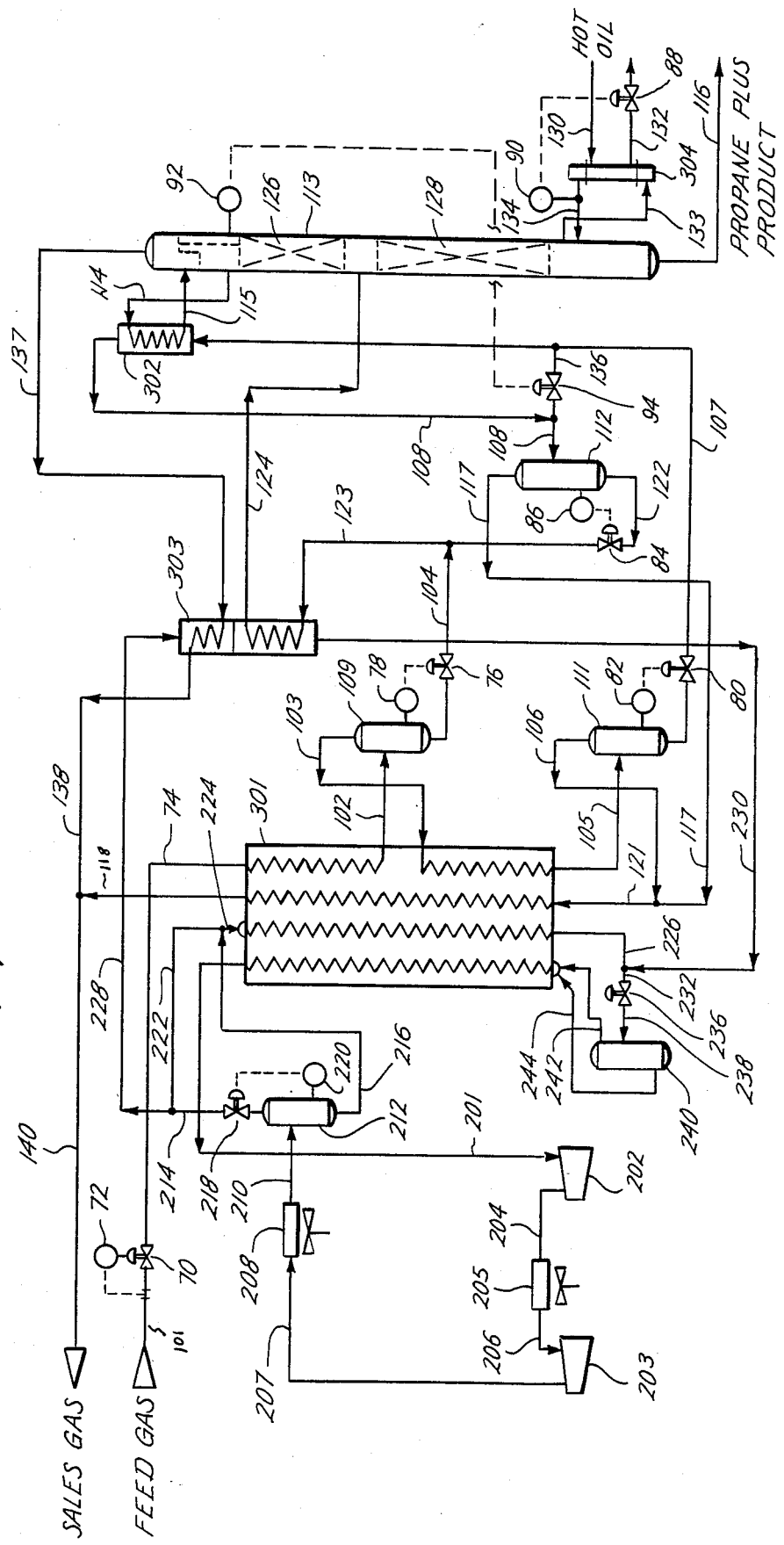

PROCESS FOR RECOVERING PROPANE AND HEAVIER HYDROCARBONS FROM A NATURAL GAS STREAM

CROSS REFERENCE TO RELATED APPLICATIONS

This application is a continuation-in-part of U.S. application Ser. No. 356,918, filed Mar. 10, 1982, by Fred Apffel, entitled "Process For Recovering Ethane, Propane and Heavier Hydrocarbons From a Natural Gas Stream" now U.S. Pat. No. 4,456,460.

TECHNICAL FIELD

The invention relates generally to processes for economically recovering valuable hydrocarbons from a natural gas stream. More specifically, it relates to an economical refrigeration process for recovering propane and heavier hydrocarbons from a natural gas stream by indirect heat exchange.

BACKGROUND ART

Natural gas is obtained from underground reservoirs and pumped through pipelines to various industrial and commercial consumers. Much of the natural gas is utilized for heating purposes and, accordingly, requires a BTU content of only 900 to 1000 BTU per m.c.f. A natural gas stream composed mainly of methane and ethane is sufficient to achieve such heating values. However, much of the natural gas obtained from underground reservoirs is rich in other components, such as propane, pentane and butane, which are heavier than methane. These components are industrially valuable in many processes, and, accordingly, separation of them from the methane and ethane prior to burning of the natural gas is highly desirable. Separation is usually accomplished at cryogenic temperature with distillation to separate and return methane and ethane to the gas pipeline while retaining a significant percentage of the propane and heavier components.

DISCLOSURE OF THE INVENTION

A process and apparatus for economically separating heavier components of a vapor stream from ethane and lighter constituents of a natural gas stream is disclosed. It uses a mixed refrigeration system using two phase flow for refrigeration to facilitate separation of ethane, methane and lighter constituents of the natural gas stream from the hydrocarbon components, such as propane and heavier gases. The separation process of the natural gas stream is accomplished in two stages. First, the inlet gas stream is cooled in exchange with refrigerant and residue gas and partially condensed. Second, the condensed mixture is fed to a fractionation tower, where the ethane, methane and lighter gases are separated from the other hydrocarbons using indirect heat exchange with the mixed refrigerant to provide the energy used for distillation.

Distillation occurs at temperatures at −120° F. to 50° F. and at pressures at 200 to 500 psia. The process uses, exclusively, an indirect refrigerant system to reduce the temperature of the feed gas stream to the desired cryogenic temperature. The refrigerant system is self contained, operating on the same basic principal as a freon or propane refrigerant and using a two stage compression scheme.

The process apparatus consist of equipment operating on the process and the refrigerant streams.

With regard to the process stream, two sets of apparatus are associated with it. The first is the cooling and condensing section and the second is the fractionation system column.

With regard to the refrigerant stream, there are four basic sets of equipment that operate on it. These are: (1) compressors; (2) bottom reboiler; (3) top exchanger; and (4) refrigerant/feed exchanger.

BRIEF DESCRIPTION OF THE DRAWINGS

For a further understanding of the nature and objects of the present invention, reference is made to the following detailed description taken in conjuction with the drawings in which like parts are given like reference numerals, and wherein:

FIG. 1 is a flow diagram of the preferred embodiment of the present invention.

DESCRIPTION OF THE PREFERRED EMBODIMENT

A process and apparatus for economically separating heavier components of a vapor stream from ethane and lighter constituents is disclosed. It uses a refrigeration system to facilitate separation of ethane and lighter constituents of a natural gas stream from the hydrocarbon components, such as propane and heavier gases. The separation process of the natural gas stream is accomplished in two stages. First, the inlet gas stream is cooled in exchange with refrigerant and residue gas. After cooling, the inlet stream is partially condensed, with part of the ethane and almost all of the heavier hydrocarbons forming the condensate stream and almost all of the methane and part of of rest of ethane forming a vapor stream. Second, the condensed mixture is fed to a fractionation tower where the residual ethane, methane and lighter gases are separated from the other hydrocarbons.

The cooling and condensation of the hydrocarbons in the feed stream is accomplished in an indirect contact exchange process with a stream of residue and refrigerant in indirect contact heat exchangers. The cooling is also accomplished by flashing of the feed stream gases.

The refrigerant utilizes a mixture of hydrocarbons, with the refrigerant process comprising of compression, condensation, expansion, and evaporation. The process uses exclusively an indirect refrigerant system to reduce the temperature of the feed gas stream to the desired temperature. The refrigerant system is self contained, operating on the same basic principal as a freon or propane refrigerant scheme. However, the refrigerant is made up of, preferably, a mixture of hydrocarbons which include methane, ethylene, propane, butanes, and pentane. The composition range of the components of the refrigerant is set out in Table I below.

TABLE I

| Refrigerant Composition Range | |
|---|---|
| | Mol % |
| Methane | 0–15 |
| Ethane | 0–60 |
| Ethylene | 15–60 |
| Propane | 10–30 |
| I—Butane | 0–5 |
| N Butane | 0–5 |
| I Pentane | 5–20 |

As noted in Table I, ethane could be used in place of or in conjunction with ethylene. The mixture may be adjusted to match the cooling and condensing characteristics of the feed gas being refrigerated and the temperature requirements.

The process apparatus consist of equipment operating on the process and the refrigerant streams.

With regard to the process stream, two sets of apparatus are associated with it. The first is the cooling and condensing section and the second is the fractionation tower.

With regard to the refrigerant stream, there are four basic sets of equipment that operate on it. These are: (1) compressors and flash systems; (2) feed exchanger; (3) top exchanger; and (4) refrigerant/feed exchanger.

A bottoms reboiler using hot oil is also used.

REFRIGERATION CYCLE

The process uses an indirect refrigerant system to reduce the feed-gas stream to the desired cryogenic temperature. The refrigerant is compressed, heat of compression removed, cooled and condensed, expanded across a valve, and evaporated as it transfers the cold energy to the feed-gas stream. Additionally, the cold or evaporating refrigerant provides part of the energy to condense and subcool the warm refrigerant to the desired temperature.

The refrigerant is made up of a mixture of hydrocarbons. These include, preferably, methane, ethylene, propane, butanes, and pentane described above. The concentration of these components may be adjusted to match the cooling and condensing characteristics of the feed gas being refrigerated and the cryogenic temperature requirement.

Additionally, the refrigerant flow rate and compression ratio may be varied to further adjust the refrigerant system. Each of the variables may be optimized to produce the most efficient, economic refrigerant design for the feed gas being processed.

The operation of the refrigerant system should be fully automated and easy to control.

In the disclosed embodiments of the present invention, the refrigeration cycle includes introducing inlet stream 201 into the suction of the first stage compressor 202 of two stages of compression 202, 203. The composition range of the inlet stream 201 to the first compression stage 202 is set out in Table I.

Each stage includes a refrigerant compressor suction scrubber (not shown), and a compressor. The sizes of the scrubbers depend upon the size of the refrigerant system. They are typically fabricated units and can be purchased from any number of vendors including Watts Company, McIver and Smith, and Taylor Tank. The compressors are preferably reciprocating compressor, such as that built by Ingersoll Rand Co., Worthington Corp. and Clark Industries. It is recognized that the compression system could also be a centrifugal compressor but with overall lower horsepower efficiency.

The first stage 202 of compression includes the compressor. The compressor should be sized to raise the stream pressure from an inlet pressure of 20–100 psia to a discharge pressure in stream 204 of 100–250 psia. The discharge 204 from the first compression in stage 202 is subsequently cooled in an air or water cooler 205 to a lower temperature of 60° F. to 125° F. The outlet stream 206 of after cooler 205 enters the second stage 203 of compression.

Second stage 203 of compression includes second stage compressor. The second stage compressor should be sized to raise the inlet 206 pressure to a pressure at the stream 207 of 200–600 psia. Stream 207 is subsequently cooled in the air or water cooler 208 where part of the components in the hydrocarbon refrigerant stream is condensed and exits the exchanger 208 in stream 210.

Those skilled in the art will recognize that there are several methods of obtaining adequate compression of refrigerant gases in a two stage process. The present invention should not be limited to any particular physical design of the two stage refrigerant system. The examples given above are given merely as illustration and are not intended to limit the scope of the invention.

The outlet stream 210 enters a liquid vapor separator 212. The vapor and liquid are separated in separator 212. The vapor and liquid streams exit separately from separator 212 as two effluent streams, vapor stream 214 and liquid stream 216. The amount of vapor in stream 214 is controlled by valve 218. This valve 218 opens and closes in response to the level in separator 212 sensed by level sensor/controller 220. The liquid is forced from the separator by the use of valve 218. A portion of the vapor stream 214 enters a side stream 222 and all of the liquid stream 216 are subsequently recombined in a header on heat exchanger 301 to form a two phase refrigerant stream 224. Stream 224 is then fed to heat exchanger 301.

Heat exchanger 301 is a multi-path process stream heat exchanger for use in exchanging energy between warm process and refrigerant streams and cold process and refrigerant streams. Exchanger 301 is, preferably, the brazed aluminum type as manufactured by the Trane Company or Stewart Warner. The passages of the exchanger are approximately 3/8 inches deep by 3 to 4 feet wide by 12 to 20 feet long. The width, length and number of passages depends on the quantity of energy being transferred and flow requirement of the process and refrigerant streams, both warm and cold. The flow of the warm and cold streams is countercurrent in each passage. The distribution of these strems is accomplished with manifolds across the depth of the passages. Those passages selected for the stream to flow through are open; the others are blocked. The selection of the stream flow paths is strategically selected to optimize heat transfer efficiency.

Refrigerant stream 224 is fed to exchanger 301 where it is condensed and subcooled to temperature level of $-20°$ F. to $-150°$ F., and exits as stream 226.

The vapor stream 228 is the stream remaining after vapor is taken from stream 214 by stream 222. Approximately twenty percent of the vapor in stream 214 is fed to stream 228 and feeds exchanger 303 where it cross-exchanges with the cold liquid in streams 123, 124 discussed infra and the vapor from fractionation 113 in streams 134, 138 discussed infra. The refrigerant exits exchanger 303 at temperatures ranging from $-20°$ F. to $-130°$ F. via stream 230 where all the hydrocarbons are totally condensed.

The cold liquids in streams 230, 226 are then recombined in stream 232.

The pressure of stream 232 is lowered substantially as the refrigerant expands across the Joule—Thompson control valve 236, where auto refrigeration occurs, thus producing temperatures from 10° F. to 30° F. colder than stream 232 and exits valve 236 via stream 238.

Stream 238 feeds the vapor-liquid separator 240 where the vapor is separated and exits the separator via stream 242. Similarly, the separted liquids exit via stream 244 and are recombined in a header attached to exchanger 301 to accomplish appropriate distribution of liquid and vapor in exchanger 301.

The vapor-liquid refrigerant from streams 242, 244, in parallel with the cold gas in stream 121 discussed infra, cross-exchange and provide the refrigerant energy for the warm refrigerant in stream 224 and the feed gas in streams 74, 103 discussed infra. The warmed refrigerant exits the exchanger 301 via inlet stream 201 to repeat the closed cycle.

PROCESS STREAM

As shown in FIG. 1, process inlet of feed gas enters the process at stream 101. The amount of gas entering the process is controlled by valve 70. Valve 70 increases its opening if the flow measured by sensor/controller 72 is lower than a predetermined set point, and decreases its opening if the flow measured by sensor/controller 72 is higher than a predetermined set point. The gas exits valve 70 in stream 74.

The typical feed gas composition range is set out in the following Table II:

TABLE II
FEED GAS RANGE OF COMPOSITION

| COMPONENT | RICH GAS MOL % | LEAN GAS MOL % |
|---|---|---|
| NITROGEN | 3.74 | .24 |
| CARBON DIOXIDE | .70 | .36 |
| METHANE | 75.52 | 92.00 |
| ETHANE | 11.60 | 4.52 |
| PROPANE | 5.05 | 1.97 |
| I—BUTANE | .63 | .24 |
| N—BUTANE | 1.48 | .31 |
| I—PETANE | .37 | .11 |
| N—PETANE | .34 | .08 |
| HEXANE | .27 | .17 |
| HEPTANE | .30 | .00 |
| TOTAL | 100.00 | 100.00 |

The pressure range of the inlet gas is 100 to 1400 psia, with a temperature range of 40° to 120° F.

After the process inlet gas enters the process, it is dehydrated (not shown) prior to entering exchanger 301.

Dehydration, or removal of any moisture that the inlet gas may contain, is imperative. Even slight amounts of water in the gas stream at the temperatures required to separate the methane and ethane from the heavier hydrocarbons will form hydrates and freeze. This will subsequently plug up the equipment and piping.

The dehydration is accomplished by processing the gas through a vessel, not shown, containing, for example, molecular sieve material. The molecular sieve material is porous and water, being a smaller molecule than the hydrocarbons, is preferentially absorbed into its pores. The gas exits the dehydration unit essentially free of moisture. The molecular sieve bed becomes saturated with water after a period of time and has to be regenerated. Therefore, two absorption vessels are required. One is always in adsorption service while the other is being regenerated.

The regeneration is achieved by recycling a slip stream of the dry residue gas. Approximately 8 to 10 percent of through-put gas is required for this purpose. The regeneration gas is compressed and heated to approximately 550° F. and processed through the dehydrator being regenerated, driving the moisture from the molecular sieve. This hot regeneration gas bearing the desorbed moisture is subsequently cooled, and the major part of the water is condensed from the gas. The water is dumped to the process sewer, and the regeneration gas is recycled to the main residue-gas stream. After the water has been removed from the molecular sieve, the heater is bypassed or turned off, and the dehydrator is cooled to ambient or inlet gas temperature, using the regeneration gas.

The absorption cycle is generally set for this type of plant at eight hours; the heating cycle at three hours; and the cooling cycle at two hours.

The stream 74 is then fed directly to the feed-refrigerant exchanger 301.

Feed stream 74 is cooled in exchanger 301, and part of the heavier hydrocarbons are condensed. Depending on feed gas composition and pressure, the feed gas is cooled to an intermediate temperature level ranging from 0° F. to −60° F. At this point a large part of the heavier hydrocarbons are condensed. This cooled and partially condensed stream is withdrawn from exchanger 301 in stream 102 which is fed to a vapor-liquid separator 109. The vapor and liquid are separated in separator 109. The vapors return to the exchanger 301 via stream 103, where they are further cooled, and where additional condensation of heavier hydrocarbons takes place.

The condensed liquid from the first vapor separator 109 exits via a stream whose flow rate is controlled by valve 76. The liquid exits valve 76 in stream 104. To prevent gas from entering stream 104, a liquid level is maintained in the feed-gas separator 109, using level control sensor/controller 78 and level control valve 76.

The vapor in stream 103 enters the refrigerant/feed exchanger 301 where it is further cooled and additional condensation takes place. The stream leaves the exchanger 301 at temperatures of −70° F. to −150° F., depending on pressure and feed gas composition, via stream 105. Stream 105 is fed to a second vapor-liquid separator 111, as is shown in FIG. 1, where the liquid and vapor in the stream 105 are separated. The vapor is recycled through stream 106 to stream 121 and thence refrigerant/feed gas exchanger 301. Refrigerant energy is recovered from the vapor in stream 121, as it flows countercurrent to the incoming feed. The vapor exits heat exchanger 301 via stream 118 and stream 140 where it leaves the battery limits of the plant.

The liquid from the second liquid-vapor separator 111 is fed to level control valve 80. The liquid level in the second liquid-vapor separator 111 is controlled by the level control instrument sensor 82 manipulating valve 80. Flow from level control valve 80 to reflux condenser 302 occurs via stream 107. Stream 107 contains cold liquid which provides reflux cooling to the refractionation tower 113. Refrigeration is accomplished by cross-exchange of energy in the reflux condenser 302, the cold liquid in stream 107 is warmed in the exchange of energy and part of the liquid contained in stream 107 is vaporized. The two phase fluid exits condenser 302 via stream 108. Stream 108 is fed to liquid-vapor separator 112 which separates the vapor and liquid of stream 108. The vapor exits separator 112 via stream 117 and is recombined with the vapor in stream 106 from separator 111, forming stream 121.

The liquid stream 122 from vapor-liquid separator 112 is fed to level control valve 84. The liquid level is the third liquid-vapor separator 112 is controlled by the level control instrument sensor 86 manipulating valve 84. Flow from level control valve 84 exits where it is recombined with stream 104 to form stream 123.

Additional refrigerant energy is recovered from stream 123 by a cross-exchange of energy with warm refrigerant in exchanger 303. The liquids from stream 123 exit exchanger 303 via stream 124 which feeds fractionation tower 113.

Fractionation tower 113 should preferably operate at pressures below 550 psia to accomplish the separation of ethane from heavier components. Therefore, where feed gases are collected and condensed above this pressure level, the level control valves 80, 84 act as expansion valves as well as level control valves. In this way, the pressure is lower to that of fractionation tower 113.

The use of an external or indirect refrigerant system and the multiple liquid-vapor separators permits the fractination tower 113 to operate at much higher pressures. The upper process pressure range for the fractionation tower 113 is usually limited to the range of 400 to 550 psia. Operating the fractionation tower at this level of pressure reduces the limits of temperature to which the feed gas must be cooled. At these pressures, a temperature of 0° to −50° F. is all that is required to liquify the ethane to meet or exceed most ethane-recovery requirements.

The fractionation tower 113 is designed with external condenser 302 and bottom reboiler 304 both of which are indirect heat exchangers. The fractionation tower 113 separates the ethane and lighter constituents from the propane and heavier hydrocarbons.

The fratination tower 113 preferably has two sets of packing 126, 128. Typically, inlet stream 124 enters fractionation tower 113 between packing 126 and packing 128.

The heavier liquid hydrocarbons exit fractionation tower 113 via stream 116. The heat to the bottom of fractionation tower 113 is provided by bottom reboiler 304, using hot oil, such as Mobil Therminol 66, feed through stream 130, exiting boiler 304 via stream 132. The output process stream 134 of reboiler 304 is connected to the bottoms of fractionation tower 113 and its input is connected to the bottoms of fractionation tower 113 by process stream 133. In the preferred embodiment, hot oil stream 130 flows countercurrent with the process stream 132. The flow of hot oil is controlled by valve 88 placed in stream 133. Temperature controller 90 placed in outlet stream 134 controls the position of valve 88 based on the temperature in stream 134.

A vapor stream 114 flows to the reflux condenser 302 from near the top of fractionation tower 113 where refrigeration is provided from stream 107 to condense parts of the vapor stream 114. The condensed liquid provides reflux that returns to the fractionation tower 113 via stream 115. This operation occurs at temperature levels of 0° F. to −50° F. The temperature at the top of fractionation tower 113 is controlled by temperature controller 92 connected to a temperature sensor near the top of the fractionation tower 113. Controller 92 manipulates valve 94, thereby controlling the amount of fluid from line 107 that is diverted from condenser 302 via a stream 136. The outlet fluid of valve 94 recombines with the two phase flow of stream 108 prior to entry into liquid-vapor separator 112.

Fractionation tower 113 may be obtained from several companies, such as Taylor Tank, Inc., McIver, and Smith Industries. The materials of construction of fractionation tower 113 are, for example, 304 stainless steel. The packings 126, 128 may be, for example, pall rings made of aluminum. The packings may be obtained from several companies, such as Glitch, Inc. and Koch Engineering.

Reboiler 304 may be, for example, the fixed tube sheet, vertical, once-through shell and tube carbon steel exchangers, such as those manufactured by Kruger Engineering and Manufacturing Company and The Thermex, Inc.

The vapor outlet of fractionation tower 113 is connected to heat exchanger 303 by stream 137. Exchanger 303 permits refrigerant energy to be recovered from the fluid in stream 134 as it flows countercurrent to refrigerant stream 228. The vapor exits heat exchanger 303 via stream 138 where it combines with stream 118 and leaves the battery limits of the plant as stream 140 which is the final product of ethane and lighter hydrocarbon gases.

The refrigeration process is an integral part of the distillation or fractionation process, providing heat energy while recovering refrigeration energy at the same time.

The distillation is accomplished by applying heat energy appropriately along the length of the distillation tower 113, while at the same time recovering refrigerant energy. The heat energy at the base of the tower 113 is from the hot oil in stream 130 entering bottom reboiler 304 and flowing countercurrent to the liquid in the bottom of tower 113 that flows to the bottom reboiler 304 in stream 133 and exits in stream 134. The material in stream 134 has two phases, vapor and liquid. The vapor flows up the tower 113; liquid exits the tower via stream 116.

EXAMPLE

The following is given as an example that illustrates, but should not limit, the present invention. The example is given in the form of Tables III and IV which shows steady state process and refrigerant flows and where the stream numbers correspond to the stream numbers of FIG. 1. The use of "V" and "L" before a stream number denotes the vapor and liquid phase of the stream respectively. The number "2" before a stream number denotes a two phase stream of liquid and vapor.

TABLE 1

| DESCRIPTION | | | 101 | 102 | 103 | 104 | 105 | 106 |
|---|---|---|---|---|---|---|---|---|
| | | | FLOW RATES LBMOL/HR (PHASE) | | | | | |
| COMP | M. W. | G/MOL | (V) | (2) | (V) | (L) | (2) | (V) |
| N2 | 28.02 | 4.17 | 21.73 | 21.73 | 21.69 | .04 | 21.69 | 21.14 |
| CO2 | 44.01 | 6.40 | 8.78 | 8.78 | 8.61 | .17 | 8.61 | 6.20 |
| CH4 | 16.04 | 6.42 | 1913.38 | 1913.38 | 1899.70 | 13.68 | 1899.70 | 1710.32 |
| C2H6 | 30.07 | 9.56 | 169.01 | 169.01 | 159.77 | 9.24 | 159.77 | 71.34 |
| C3H8 | 44.09 | 10.45 | 52.02 | 52.02 | 41.15 | 10.87 | 41.15 | 4.83 |
| IC4H10 | 58.12 | 12.41 | 6.15 | 6.15 | 3.47 | 2.67 | 3.47 | .12 |

TABLE 1-continued

| DESCRIPTION | | | 101 | 102 | 103 | 104 | 105 | 106 |
|---|---|---|---|---|---|---|---|---|
| NC4H10 | 58.12 | 11.95 | 13.39 | 13.39 | 6.10 | 7.29 | 6.10 | .13 |
| IC5H12 | 72.15 | 13.88 | 3.29 | 3.29 | .72 | 2.57 | .72 | .00 |
| NC5H12 | 72.15 | 13.74 | 4.17 | 4.17 | .68 | 3.50 | .68 | .00 |
| NC6H14 | 86.17 | 15.56 | 3.07 | 3.07 | .14 | 2.94 | .14 | .00 |
| TOTAL | | | 2195.00 | 2195.00 | 2142.03 | 52.97 | 2142.03 | 1814.08 |
| TEMPERATURE | DEG F | | 100.0 | −30.0 | −30.0 | −30.0 | −150.0 | −105.0 |
| PRESSURE | PSIA | | 450.0 | 445.0 | 445.0 | 445.0 | 440.0 | 440.0 |
| TOTAL ENTHAL | MMBTU/HR | | 9.730 | 6.359 | 6.495 | −.135 | 3.510 | 4.024 |
| SPECF ENTHAL | BTU/LB | | 237.28 | 155.09 | 167.61 | −59.90 | 90.58 | 131.18 |
| PSEUDO TC | DEG F | | −87.1 | −87.1 | −93.0 | 152.6 | −93.0 | −108.1 |
| PSEUDO PC | PSIA | | 672.3 | 672.3 | 673.8 | 611.0 | 673.8 | 673.6 |
| PSEUDO TR | | | 1.502 | 1.153 | 1.172 | .702 | .967 | 1.009 |
| PSEUDO PR | | | .669 | .662 | .660 | .728 | .653 | .653 |
| PSEUDO ACENT | | | .020 | .020 | .017 | .129 | .017 | .011 |
| LVOL/MOL @ 60F | GAL/MOL | | 0.00 | 0.00 | 0.00 | 10.21 | 0.00 | 0.00 |
| STP GAS VOL | MMSCFD | | 20.055 | 0.000 | 19.571 | 0.000 | 0.000 | 16.574 |
| DENSITY @ T,P | LB/CUFT | | 1.4907 | 0.0000 | 1.8500 | 32.3499 | 0.0000 | 2.0504 |
| SPEC GRAV | | | .6448 | 0.0000 | .6244 | .5003 | 0.0000 | .5837 |
| LVOL/MIN @ 60F | GAL/MIN | | 0.00 | 0.00 | 0.00 | 9.01 | 0.00 | 0.00 |
| LVOL/MIN @ T,P | GAL/MIN | | 0.00 | 0.00 | 0.00 | 8.69 | 0.00 | 0.00 |
| GVOL/MIN @ T,P | CUFT/MIN | | 458.45 | 0.00 | 349.10 | 0.00 | 0.00 | 249.34 |
| Z(SRK) | | | .9388 | 0.0000 | .9435 | .1289 | 0.0000 | .9532 |
| MASS | LB | | 41004.1 | 41004.1 | 38748.6 | 2255.5 | 38748.6 | 30675.1 |
| MOL WT | LB/LBMOL | | 18.681 | 18.681 | 18.090 | 42.577 | 18.090 | 16.909 |

TABLE 2

| DESCRIPTION | | | 107 | 108 | 117 | 122 | 123 | 124 |
|---|---|---|---|---|---|---|---|---|
| | | | FLOW RATES LBMOL/HR (PHASE) | | | | | |
| COMP | M. W. | G/MOL | (L) | (2) | (V) | (L) | (2) | (2) |
| N2 | 28.02 | 4.17 | .55 | .55 | .48 | .08 | .12 | .12 |
| CO2 | 44.01 | 6.40 | 2.41 | 2.41 | .81 | 1.60 | 1.77 | 1.77 |
| CH4 | 16.04 | 6.42 | 189.38 | 189.38 | 114.80 | 74.58 | 88.25 | 88.25 |
| C2H6 | 30.07 | 9.56 | 88.44 | 88.44 | 12.55 | 75.88 | 85.12 | 85.12 |
| C3H8 | 44.09 | 10.45 | 36.32 | 36.32 | 1.12 | 35.21 | 46.08 | 46.08 |
| IC4H10 | 58.12 | 12.41 | 3.35 | 3.35 | .03 | 3.32 | 5.99 | 5.99 |
| NC4H10 | 58.12 | 11.95 | 5.96 | 5.96 | .04 | 5.93 | 13.22 | 13.22 |
| IC5H12 | 72.15 | 13.88 | .72 | .72 | .00 | .71 | 3.29 | 3.29 |
| NC5H12 | 72.15 | 13.74 | .67 | .67 | .00 | .67 | 4.17 | 4.17 |
| NC6H14 | 86.17 | 15.56 | .14 | .14 | .00 | .14 | 3.07 | 3.07 |
| TOTAL | | | 327.94 | 327.94 | 129.83 | 198.11 | 251.08 | 251.08 |
| TEMPERATURE | DEG F | | −105.0 | −70.0 | −70.0 | −70.0 | −62.0 | −10.0 |
| PRESSURE | PSIA | | 440.0 | 435.0 | 435.0 | 435.0 | 430.0 | 425.0 |
| TOTAL ENTHAL | MMBTU/HR | | −.514 | −.026 | .336 | −.362 | −.495 | −.060 |
| SPECF ENTHAL | BTU/LB | | −63.68 | −3.23 | 144.83 | −62.98 | −61.86 | −7.48 |
| PSEUDO TC | DEG F | | −9.7 | −9.7 | −92.6 | 44.7 | 67.5 | 67.5 |
| PSEUDO PC | PSIA | | 674.9 | 674.9 | 677.9 | 672.9 | 659.8 | 659.8 |
| PSEUDO TR | | | .788 | .866 | 1.062 | .773 | .754 | .853 |
| PSEUDO PR | | | .652 | .645 | .642 | .646 | .652 | .644 |
| PSEUDO ACENT | | | .053 | .053 | .017 | .077 | .088 | .088 |
| LVOL/MOL @ 60F | GAL/MOL | | 7.91 | 0.00 | 0.00 | 8.66 | 0.00 | 0.00 |
| STP GAS VOL | MMSCFD | | 0.000 | 0.000 | 1.186 | 0.000 | 0.000 | 0.000 |
| DENSITY @ T,P | LB/CUFT | | 25.5143 | 0.0000 | 1.9697 | 26.7149 | 0.0000 | 0.0000 |
| SPEC GRAV | | | .3735 | 0.0000 | .6172 | .4021 | 0.0000 | 0.0000 |
| LVOL/MIN @ 60F | GAL/MIN | | 43.21 | 0.00 | 0.00 | 28.60 | 0.00 | 0.0 |
| LVOL/MIN @ T,P | GAL/MIN | | 39.45 | 0.00 | 0.00 | 26.85 | 0.00 | 0.0 |
| GVOL/MIN @ T,P | CUFT/MIN | | 0.00 | 0.00 | 19.64 | 0.00 | 0.00 | 0.0 |
| Z(SRK) | | | .8723 | 0.0000 | .9442 | .8023 | 0.0000 | 0.0000 |
| MASS | LB | | 8073.5 | 8073.5 | 2321.5 | 5752.0 | 8007.5 | 8007.5 |
| MOL WT | LB/LBMOL | | 24.619 | 24.619 | 17.881 | 29.034 | 31.892 | 31.892 |

TABLE 3

| DESCRIPTION | | | 137 | 114 | 115 | 116 | 138 | 118 |
|---|---|---|---|---|---|---|---|---|
| | | | FLOW RATES LBMOL/HR (PHASE) | | | | | |
| COMP | M. W. | G/MOL | (V) | (V) | (2) | (L) | (V) | (V) |
| N2 | 28.02 | 4.17 | .12 | .13 | .13 | .00 | .12 | 21.6 |
| C02 | 44.01 | 6.40 | 1.77 | 2.75 | 2.75 | .00 | 1.77 | 7.0 |
| CH4 | 16.04 | 6.42 | 88.25 | 111.44 | 111.44 | .00 | 88.25 | 1825.13 |
| C2H6 | 30.07 | 9.56 | 83.99 | 197.39 | 197.39 | 1.13 | 83.99 | 83.8 |
| C3H8 | 44.09 | 10.45 | .57 | 3.21 | 3.21 | 45.51 | .57 | 5.94 |
| IC4H10 | 58.12 | 12.41 | .00 | .00 | .00 | 5.99 | .00 | .15 |
| NC4H10 | 58.12 | 11.95 | .00 | .0* | .0* | 13.22 | .00 | .17 |
| IC5H12 | 72.15 | 13.88 | .00 | .0* | .0* | 3.29 | .00 | .0 |

TABLE 3-continued

| DESCRIPTION | | | 137 | 114 | 115 | 116 | 138 | 118 |
|---|---|---|---|---|---|---|---|---|
| NC5H12 | 72.15 | 13.74 | .00 | .0* | .0* | 4.17 | .00 | .00 |
| NC6H14 | 86.17 | 15.56 | .00 | .0* | .0* | 3.07 | .00 | .0* |
| TOTAL | | | 174.70 | 314.91 | 314.91 | 76.38 | 174.70 | 1943.92 |
| TEMPERATURE | DEG F | | −10.5 | 10.8 | −10.5 | 211.5 | 110.0 | −102.0 |
| PRESSURE | PSIA | | 425.0 | 425.0 | 425.0 | 430.0 | 420.0 | 430.0 |
| TOTAL ENTHAL | MMBTU/HR | | .545 | 1.048 | .441 | .325 | .817 | 4.409 |
| SPECF ENTHAL | BTU/LB | | 134.59 | 131.19 | 55.25 | 82.04 | 201.77 | 133.61 |
| PSEUDO TC | DEG F | | −14.0 | 18.2 | 18.2 | 253.9 | −14.0 | −107.0 |
| PSEUDO PC | PSIA | | 694.5 | 698.9 | 698.9 | 580.6 | 694.5 | 673.9 |
| PSEUDO TR | | | 1.008 | .985 | .940 | .941 | 1.278 | 1.014 |
| PSEUDO PR | | | .612 | .608 | .608 | .741 | .605 | .638 |
| PSEUDO ACENT | | | .051 | .064 | .064 | .174 | .051 | .011 |
| LVOL/MOL @ 60F | GAL/MOL | | 0.00 | 0.00 | 0.00 | 11.38 | 0.00 | 0.00 |
| STP GAS VOL | MMSCFD | | 1.596 | 2.877 | 0.000 | 0.000 | 1.596 | 17.761 |
| DENSITY @ T,P | LB/CUFT | | 2.3043 | 2.4991 | 0.0000 | 33.1483 | 1.7955 | 1.9958 |
| SPEC GRAV | | | .7997 | .8757 | 0.0000 | .5464 | .7997 | .5859 |
| LVOL/MIN @ 60F | GAL/MIN | | 0.00 | 0.00 | 0.00 | 14.49 | 0.00 | 0.00 |
| LVOL/MIN @ T,P | GAL/MIN | | 0.00 | 0.00 | 0.00 | 14.89 | 0.00 | 0.00 |
| GVOL/MIN @ T,P | CUFT/MIN | | 29.28 | 53.28 | 0.00 | 0.00 | 37.57 | 275.54 |
| Z(SRK) | | | .8863 | .8543 | 0.0000 | .1277 | .8863 | .9526 |
| MASS | LB | | 4047.6 | 7988.9 | 7988.9 | 3959.9 | 4047.6 | 32996.6 |
| MOL WT | LB/lBMOL | | 23.168 | 25.369 | 25.369 | 51.845 | 23.168 | 16.974 |

TABLE 4

| DESCRIPTION | | | 201 | 204 | 206 | 207 | 210 | 214 |
|---|---|---|---|---|---|---|---|---|
| | | | FLOW RATES LBMOL/HR (PHASE) | | | | | |
| COMP | M. W. | G/MOL | (V) | (V) | (V) | (V) | (2) | (V) |
| CH4 | 16.04 | 6.42 | 59.28 | 59.28 | 59.28 | 59.28 | 59.28 | 55.16 |
| C2H4 | 28.05 | 9.66 | 212.16 | 212.16 | 212.16 | 212.16 | 212.16 | 178.48 |
| C2H6 | 30.07 | 9.56 | 14.56 | 14.56 | 14.56 | 14.56 | 14.56 | 11.64 |
| C3H8 | 44.09 | 10.45 | 130.00 | 130.00 | 130.00 | 130.00 | 130.00 | 80.42 |
| IC4H10 | 58.12 | 12.41 | 13.52 | 13.52 | 13.52 | 13.52 | 13.52 | 6.18 |
| NC4H10 | 58.12 | 11.95 | 13.52 | 13.52 | 13.52 | 13.52 | 13.52 | 5.37 |
| IC5H12 | 72.15 | 13.88 | 86.32 | 86.32 | 86.32 | 86.32 | 86.32 | 21.75 |
| TOTAL | | | 529.36 | 529.36 | 529.36 | 529.36 | 529.36 | 359.01 |
| TEMPERATURE | DEG F | | 110.0 | 207.5 | 120.0 | 224.1 | 120.0 | 120 |
| PRESSURE | PSIA | | 40.0 | 125.0 | 121.0 | 365.0 | 360.0 | 360.0 |
| TOTAL ENTHAL | MMBTU/HR | | 3.386 | 4.233 | 3.374 | 4.157 | 2.018 | 1.882 |
| SPECF ENTHAL | BTU/LB | | 162.23 | 202.82 | 161.66 | 199.15 | 96.67 | 156.47 |
| PSEUDO TC | DEG F | | 134.5 | 134.5 | 134.5 | 134.5 | 134.5 | 87.0 |
| PSEUDO PC | PSIA | | 647.0 | 647.0 | 647.0 | 647.0 | 647.0 | 675.1 |
| PSEUDO TR | | | .959 | 1.123 | .976 | 1.151 | .976 | 1.060 |
| PSEUDO PR | | | .062 | .193 | .187 | .564 | .556 | .533 |
| PSEUDO ACENT | | | .121 | .121 | .121 | .121 | .121 | .100 |
| LVOL/MOL @ 60F | GAL/MOL | | 0.00 | 0.00 | 0.00 | 0.00 | 0.00 | 0.00 |
| STP GAS VOL | MMSCFD | | 4.837 | 4.837 | 4.837 | 4.837 | 0.000 | 3.280 |
| DENSITY @ T,P | LB/CUFT | | .3021 | .8060 | .8980 | 2.2963 | 0.0000 | 2.1516 |
| SPEC GRAV | | | 1.3610 | 1.3610 | 1.3610 | 1.3610 | 0.0000 | 1.1566 |
| LVOL/MIN @ 60F | GAL/MIN | | 0.00 | 0.00 | 0.00 | 0.00 | 0.00 | 0.00 |
| LVOL/MIN @ T,P | GAL/MIN | | 0.00 | 0.00 | 0.00 | 0.00 | 0.00 | 0.00 |
| GVOL/MIN @ T,P | CUFT/MIN | | 1151.62 | 431.58 | 387.38 | 151.49 | 0.00 | 93.18 |
| Z(SRK) | | | .8539 | .8539 | .8539 | .8539 | 0.0000 | .9010 |
| MASS | LB | | 20872.1 | 20872.1 | 20872.1 | 20872.1 | 20872.1 | 12028.7 |
| MOL WT | LB/LBMOL | | 39.429 | 39.429 | 39.429 | 39.429 | 39.429 | 33.506 |

TABLE 5

| DESCRIPTION | | | 222 | 228 | 216 | 230 | 224 | 226 |
|---|---|---|---|---|---|---|---|---|
| | | | FLOW RATES lBMOL/HR (PHASE) | | | | | |
| COMP | M. W. | G/MOL | (V) | (V) | (L) | (V) | (2) | (L) |
| CH4 | 16.04 | 6.42 | 41.33 | 13.83 | 4.12 | 13.83 | 45.45 | 45.45 |
| C2H4 | 28.05 | 9.66 | 133.73 | 44.74 | 33.68 | 44.74 | 167.42 | 167.42 |
| C2H6 | 30.07 | 9.56 | 8.72 | 2.92 | 2.92 | 2.92 | 11.64 | 11.64 |
| C3H8 | 44.09 | 10.45 | 60.26 | 20.16 | 49.58 | 20.16 | 109.84 | 109.84 |
| IC4H10 | 58.12 | 12.41 | 4.63 | 1.55 | 7.34 | 1.55 | 11.97 | 11.97 |
| NC4H10 | 58.12 | 11.95 | 4.03 | 1.35 | 8.15 | 1.35 | 12.17 | 12.17 |
| IC5H12 | 72.15 | 13.88 | 16.30 | 5.45 | 64.57 | 5.45 | 80.87 | 80.87 |
| TOTAL | | | 269.00 | 90.00 | 170.35 | 90.00 | 439.36 | 439.36 |
| TEMPERATURE | DEG F | | 120.0 | 120.0 | 120.0 | −52.0 | 120.0 | −105.0 |
| PRESSURE | PSIA | | 360.0 | 360.0 | 360.0 | 355.0 | 360.0 | 355.0 |
| TOTAL ENTHAL | MMBTU/HR | | 1.410 | .4472 | .136 | −.209 | 1.546 | −1.889 |
| SPECF ENTHAL | BTU/LB | | 156.47 | 156.47 | 15.34 | −69.18 | 86.57 | −105.78 |
| PSEUDO TC | DEG F | | 87.0 | 87.0 | 234.7 | 87.0 | 144.3 | 144.3 |

TABLE 5-continued

| DESCRIPTION | | 222 | 228 | 216 | 230 | 224 | 226 |
|---|---|---|---|---|---|---|---|
| PSEUDO PC | PSIA | 675.1 | 675.1 | 587.6 | 675.1 | 641.2 | 641.2 |
| PSEUDO TR | | 1.060 | 1.060 | .835 | .746 | .960 | .587 |
| PSEUDO PR | | .533 | .533 | .613 | .526 | .561 | .554 |
| PSEUDO ACENT | | .100 | .100 | .165 | .100 | .125 | .125 |
| LVOL/MOL @ 60F | GAL/MOL | 0.00 | 0.00 | 11.64 | 9.67 | 0.00 | 10.43 |
| STP GAS VOL | MMSCFD | 2.458 | .822 | 0.000 | 0.000 | 0.000 | 0.000 |
| DENSITY @ T,P | LB/CUFT | 2.1515 | 2.1515 | 33.1251 | 27.1867 | 0.0000 | 30.7600 |
| SPEC GRAV | | 1.1565 | 1.1565 | .5351 | .4154 | 0.0000 | .4672 |
| LVOL/MIN @ 60F | GAL/MIN | 0.00 | 0.00 | 33.04 | 14.51 | 0.00 | 76.41 |
| LVOL/MIN @ T,P | GAL/MIN | 0.00 | 0.00 | 33.29 | 13.83 | 0.00 | 72.38 |
| GVOL/MIN @ T,P | CUFT/MIN | 69.82 | 23.36 | 0.00 | 0.00 | 0.00 | 0.00 |
| Z(SRK) | | .9010 | .9010 | .6906 | .9010 | 0.0000 | .8425 |
| MASS | LB | 9013.0 | 3015.6 | 8843.4 | 3015.6 | 17856.3 | 17856.3 |
| MOL WT | LB/LBMOL | 33.505 | 33.505 | 51.912 | 33.505 | 40.642 | 40.6 |

TABLE 6

| DESCRIPTION | | | 232 | 238 | 242 | 244 |
|---|---|---|---|---|---|---|
| | | | RATES LBMOL/HR (PHASE) | | | |
| COMP | M. W. | G/MOL | (L) | (2) | (V) | (L) |
| CH4 | 16.04 | 6.42 | 59.28 | 59.28 | 39.40 | 19.88 |
| C2H4 | 28.05 | 9.66 | 212.16 | 212.16 | 26.20 | 185.96 |
| C2H6 | 30.07 | 9.56 | 14.56 | 14.56 | .91 | 13.65 |
| C3H8 | 44.09 | 10.45 | 130.00 | 130.00 | .73 | 129.27 |
| IC4H10 | 58.12 | 12.41 | 13.52 | 13.52 | .01 | 13.51 |
| NC4H10 | 58.12 | 11.95 | 13.52 | 13.52 | .01 | 13.51 |
| IC5H12 | 72.15 | 13.88 | 86.32 | 86.32 | .01 | 86.31 |
| TOTAL | | | 529.36 | 529.36 | 67.26 | 462.10 |
| TEMPERATURE | DEG F | | −95.0 | −117.6 | −117.6 | −117.6 |
| PRESSURE | PSIA | | 355.0 | 45.0 | 45.0 | 45.0 |
| TOTAL ENTHAL | MMBTU/HR | | −2.084 | −2.084 | .173 | −2.257 |
| SPECF ENTHAL | BTU/LB | | −99.82 | −99.82 | 121.21 | −116.06 |
| PSEUDO TC | DEG F | | 134.5 | 134.5 | −45.8 | 160.8 |
| PSEUDO PC | PSIA | | 647.0 | 647.0 | 695.4 | 639.9 |
| PSEUDO TR | | | .614 | .576 | .827 | .551 |
| PSEUDO PR | | | .549 | .070 | .065 | .070 |
| PSEUDO ACENT | | | .121 | .121 | .040 | .132 |
| LVOL/MOL @ 60F | GAL/MOL | | 10.31 | 0.00 | 0.00 | 10.67 |
| STP GAS VOL | | 0.000 | 0.000 | 0.000 | .615 | 0.000 |
| DENSITY @ T,P | LB/CUFT | | 30.1840 | 0.0000 | .2684 | 31.0913 |
| SPEC GRAV | | | .4589 | 0.0000 | .7329 | .4728 |
| LVOL/MIN @ 60F | GAL/MIN | | 90.92 | 0.00 | 0.00 | 82.21 |
| LVOL/MIN @ T,P | GAL/MIN | | 86.22 | 0.00 | 0.00 | 77.98 |
| GVOL/MIN @ T,P | CUFT/MIN | | 0.00 | 0.00 | 88.67 | 0.00 |
| Z(SRK) | | | .8539 | 0.0000 | .9694 | .8271 |
| MASS | LB | | 20872.1 | 20872.1 | 1428.0 | 19444.1 |
| MOL WT | LB/LBMOL | | 39.429 | 39.429 | 21.231 | 42.078 |

Because many varying and different embodiments may be made within the scope of the inventive concept herein taught including equivalent structures or materials hereafter thought of, and because many modifications may be made in the embodiments herein detailed in accordance with the descriptive requirements of the law, it is to be understood that the details herein are to be interpreted as illustrative and not in a limiting sense.

What is claimed as invention is:

1. A process for separating ethane and lighter components from substantial amounts of heavier naturally occurring hydrocarbons in a mixed gas, comprising:
   A. Cooling the mixed gas inlet stream in an indirect heat exchanger with a mixed component refrigerant having at least three components with boiling points corresponding to the condensing points of the heavier hydrocarbons of the mixed gas;
   B. Separating a portion of the ethane and lighter components from the propane and heavier components through a series of intermediate separation stages;
   C. Cooling the mixed gas intermediate stream in an indirect heat exchanger with such refrigerant;
   D. Separating the ethane and lighter components from substantial amounts of heavier naturally occurring hydrocarbons of the mixed gas in a distillation column using a liquid lighter component portion as a second refrigerant to provide cooling for the intermediate mixed gas in indirect heat exchange; and
   E. Controlling the amount of cooling of such mixed gas intermediate stream by such liquid lighter component portion of the distillation column by the temperature of such liquid lighter component portion of the distillation column, the set point of the temperature being set for propane recovery.

2. The process of claim 1, wherein the refrigerant system is closed and consists of:

| COMPONENT | MOL % |
|---|---|
| Methane | 0–15 |
| Ethane | 0–60 |
| Ethylene | 15–60 |
| Propane | 10–30 |
| I—Butane | 0–5 |
| N—Butane | 0–5 |
| I—Pentane | 5–20 | and the separation of the ethane and lighter components from substantial amounts of heavier hydrocarbons of the mixed gas occurs in the distillation column at a pressure below 550 psia and a temperature of 0° F. to −50° F.

3. The process of claim 2, wherein there is further included the steps of:

F. Compressing the refrigerant prior to Step A;

G. Splitting the compressed refrigerant from Step F into two portions of the same composition;

H. Supplying a first portion of the compressed refrigerant of Step F for cooling in Step A;

I. Supplying a second portion of the compressed refrigerant of Step F to provide heat energy for the cooling of the mixed gas intermediate stream entering the distillation of Step D prior to the cooling in Step A;

J. Supplying the second portion of the compressed refrigerant of Step I for cooling in Step A;

K. Combining the first and second portion of the compressed refrigerant; and

L. Feeding the combined portions of the compressed refrigerant of Step K to the compressing Step F.

4. A process for separating ethane and lighter components from substantial amounts of heavier hydrocarbons in a mixed gas, comprising:

A. Cooling the mixed gas in a indirect heat exchanger with a mixed refrigerant;

B. Compressing the refrigerant;

C. Separating the ethane and lighter components from substantial amounts of heavier hydrocarbons of the mixed gas in a distillation column, the sole heat energy source for the distillation column coming from a media other than the compressed refrigerant;

D. Splitting the compressed refrigerant from Step B into two portions;

E. Supplying a first portion of the compressed refrigerant of Step D for cooling in Step A;

F. Supplying a second portion of the compressed refrigerant of Step D to provide heat energy for cooling of the mixed gas after Step A and prior to distillation;

G. Supplying the second portion of the compressed refrigerant of Step F for cooling in Step A;

H. Combining the first portion of the compressed refrigerant of Step E with the second portion of the compressed refrigerant of Step G; and I. Feeding the combined portions of the refrigerant to Step B.

5. A process for separating ethane and lighter components from substantial amounts of heavier hydrocarbons in a mixed gas, comprising:

A. Cooling the mixed gas in an indirect heat exchanger with a refrigerant having:

| COMPONENT | MOL % |
|---|---|
| Methane | 0–15 |
| Ethane | 0–60 |
| Ethylene | 15–60 |
| Propane | 10–30 |
| I—Butane | 0–5 |
| N—Butane | 0–5 |
| I—Pentane | 5–20 |

B. Separating the ethane and lighter components from substantial amounts of heavier hydrocarbons of the mixed gas in a distillation column with a source of heat energy other than the refrigerant.

6. The process of claim 5 wherein Step B is performed at a pressure of less than 550 psia and a temperature of 0° F. to −50° F.

* * * * *